(12) United States Patent
Limaye et al.

(10) Patent No.: US 11,376,371 B2
(45) Date of Patent: Jul. 5, 2022

(54) PEN NEEDLE PACKAGING

(71) Applicant: Embecta Corp., Andover, MA (US)

(72) Inventors: Amit Limaye, Wayne, NJ (US);
Yvonne Yan Wang, Shanghai (CN);
Joshua Herr, Cary, NC (US);
Abhijitsinh S. Raj, Morris Plains, NJ (US); James Bates, Sparta, NJ (US);
Robert Banik, Edgewater, NJ (US)

(73) Assignee: Embecta Corp., Andover, MA (US)

( * ) Notice: Subject to any disclaimer, the term of this patent is extended or adjusted under 35 U.S.C. 154(b) by 893 days.

(21) Appl. No.: 15/994,725

(22) Filed: May 31, 2018

(65) Prior Publication Data

US 2018/0289898 A1 Oct. 11, 2018

Related U.S. Application Data

(62) Division of application No. 14/655,712, filed as application No. PCT/US2013/077699 on Dec. 24, 2013, now Pat. No. 10,010,680.

(60) Provisional application No. 61/746,104, filed on Dec. 26, 2012, provisional application No. 61/746,105, filed on Dec. 26, 2012, provisional application No. 61/746,102, filed on Dec. 26, 2012, provisional application No. 61/751,333, filed on Jan. 11, 2013.

(51) Int. Cl.
| | |
|---|---|
| *A61M 5/32* | (2006.01) |
| *A61B 50/30* | (2016.01) |
| *A61B 50/36* | (2016.01) |
| *A61M 5/00* | (2006.01) |
| *A61B 50/00* | (2016.01) |

(52) U.S. Cl.
CPC ....... *A61M 5/3202* (2013.01); *A61B 50/3001* (2016.02); *A61B 50/362* (2016.02); *A61M 5/002* (2013.01); *A61M 5/321* (2013.01); *A61M 5/3293* (2013.01); *A61B 2050/0062* (2016.02); *A61B 2050/3006* (2016.02); *A61M 5/3213* (2013.01); *A61M 2005/3254* (2013.01)

(58) Field of Classification Search
CPC .... A61M 5/3202; A61M 5/002; A61M 5/321; A61M 5/3293; A61M 5/3213; A61M 2005/3254
See application file for complete search history.

(56) References Cited

U.S. PATENT DOCUMENTS

| | | | |
|---|---|---|---|
| 691,695 A | 1/1902 | Aderer et al. | |
| 1,071,797 A | 9/1913 | Roche | |
| 2,387,724 A | 10/1945 | Elman et al. | |
| 2,528,819 A | 11/1950 | Cohn et al. | |

(Continued)

FOREIGN PATENT DOCUMENTS

| | | |
|---|---|---|
| DE | 8811596 U1 | 2/1990 |
| EP | 0255215 A2 | 2/1988 |

(Continued)

*Primary Examiner* — Jacob K Ackun
(74) *Attorney, Agent, or Firm* — Greenberg Traurig, LLP; David J. Dykeman; Roman Fayerberg

(57) ABSTRACT

A disposable pen needle, comprising a hub having a needle situated thereon having a patient end and a non-patient end, a removable patient end cap attached at the distal end of the hub, a removable non-patient end cap attached at the proximal end of the hub, wherein greater force is required to detach the patient end cap than is required to detach the non-patient end cap.

13 Claims, 13 Drawing Sheets

(56) References Cited

U.S. PATENT DOCUMENTS

| | | |
|---|---|---|
| 2,962,155 A | 11/1960 | Rusciano |
| 4,610,667 A | 9/1986 | Pedicano et al. |
| 4,927,019 A | 5/1990 | Haber et al. |
| 5,222,947 A | 6/1993 | D'Amico |
| 5,242,422 A | 9/1993 | Schneberger et al. |
| 5,409,117 A | 4/1995 | Meador |
| 5,941,857 A | 8/1999 | Nguyen et al. |
| 5,971,966 A | 10/1999 | Lav |
| 7,134,550 B2 | 11/2006 | Groth |
| 7,762,994 B2 | 7/2010 | Klint et al. |
| 7,871,397 B2 | 1/2011 | Schraga |
| 8,133,200 B2 | 3/2012 | Dibiasi et al. |
| 8,287,492 B2 | 10/2012 | Schraga |
| 8,287,501 B2 | 10/2012 | Wei |
| 8,834,415 B2 | 9/2014 | Schraga |
| 8,858,507 B2 | 10/2014 | Nielsen |
| 8,998,876 B2 * | 4/2015 | Drunk ................ A61M 5/2448 604/232 |
| 9,849,243 B2 * | 12/2017 | Marshall ............. A61M 5/2033 |
| 2003/0015444 A1 | 1/2003 | Molin et al. |
| 2003/0199822 A1 | 10/2003 | Alohas et al. |
| 2003/0229315 A1 | 12/2003 | Leong et al. |
| 2008/0179207 A1 | 7/2008 | Stowe et al. |
| 2010/0063457 A1 | 3/2010 | Crossman |
| 2011/0071475 A1 | 3/2011 | Horvath et al. |
| 2012/0016300 A1 | 1/2012 | Ruan |
| 2012/0041381 A1 | 2/2012 | Raj et al. |
| 2012/0041390 A1 | 2/2012 | Spool et al. |
| 2013/0105345 A1 | 5/2013 | Van Der Beek et al. |
| 2015/0011974 A1 | 1/2015 | Schraga |
| 2015/0297837 A1 | 10/2015 | Schraga |
| 2016/0271339 A1 * | 9/2016 | Roberts ............... A61M 5/3213 |
| 2017/0049970 A1 * | 2/2017 | Dunne ................ A61M 5/326 |

FOREIGN PATENT DOCUMENTS

| | | |
|---|---|---|
| EP | 1138336 A1 | 10/2001 |
| EP | 1380316 A1 | 1/2004 |
| EP | 2033672 A2 | 3/2009 |
| EP | 2201976 A1 | 6/2010 |
| EP | 2517746 A1 | 10/2012 |
| JP | 2002-514940 | 5/2002 |
| JP | 2007-526002 | 9/2007 |
| JP | 2012-050819 A | 3/2012 |
| JP | 2012-517280 | 8/2012 |
| JP | 2012-517281 A | 8/2012 |
| JP | 2012-517282 A | 8/2012 |
| JP | 2012-232136 | 11/2012 |
| WO | WO-00/54691 A1 | 9/2000 |
| WO | WO-2010/024950 A1 | 3/2010 |
| WO | WO-2010/090734 A1 | 8/2010 |
| WO | WO-2010/102067 A2 | 9/2010 |
| WO | WO-2015/085031 A1 | 6/2015 |
| WO | WO-2016/020655 A2 | 2/2016 |

\* cited by examiner

PEN NEEDLE PACKAGING

This application is a division of U.S. Nonprovisional application Ser. No. 14/655,712, filed Jun. 25, 2015, which is a national stage application, filed under 35 U.S.C. § 371, of International Application No. PCT/US2013/077699, filed Dec. 24, 2013 which claims the benefit under 35 U.S.C. § 119(e) of U.S. Provisional Application No. 61/746,104, filed Dec. 26, 2012, No. 61/746,105, filed Dec. 26, 2012, No. 61/746,102, filed Dec. 26, 2012 and No. 61/751,333, filed Jan. 11, 2013, all of which are incorporated by reference.

BACKGROUND OF THE INVENTION

Field of the Invention

The invention is in the field of sterile packaging for a pen needle. In particular, the disclosure pertains to sterile containers for a pen needle which can be opened by the user with one hand, without removing a heat sealed paper-foil label, and/or manipulated to install the pen needle on a medication pen without separately handling the pen needle. In embodiments, the packaging serves as a sharps container after use.

Description of the Related Art

Pen needles are widely used in medication delivery systems for self-administered injectable drugs. The pen needle is a separate unit from the medication pen which contains the medication and it is transported and sold in sterile packaging. In the packaging commonly used, the pen needle is shielded with an "inner shield" covering the needle. The needle-bearing hub and the inner shield are then packaged into an "outer shield" which contains the pen needle. A paper-foil peel off label (sometimes referred to as a "teardrop label") provides sterile closure to the container. Although such containers are widely used, it is desirable to simplify the packaging and improve the product in terms of ease of use, so that it can be opened with one hand, for example, and without handling the pen needle prior to installing the pen needle on a medication pen.

United States Patent Application Publication No. 2012/0016300 describes a pen needle assembly having a hub with a needle thereon which is received in an outer cover. The cover is provided with a locking member for locking the needle in the outer cover. In embodiments, the needle is secured in the outer cover with a cap, attached to the hub by a hinge.

U.S. Pat. No. 8,133,200 describes a reversible cap for a pen needle which connects to an outer cover of the pen needle in a first position before the needle is used and in a second position after the needle is used. In embodiments, the cap is removable in the first position and locked to the outer cover in the second position.

International Application No. WO 2010/090734 describes a pen needle assembly, comprising a hub with a needle fixed thereon; a cover member covering a first end of the needle; and a sealing member for covering a second end of the needle. One or more of the hub, cover member and the sealing member are made of a biodegradable material. Although closures are provided on opposite ends of the pen needle, sterility is maintained using an "inner shield" over the patient end of the needle in the packaging.

Notwithstanding the improvements described in the aforesaid related art, it is still desirable to improve the known pen needle assemblies and sterile packaging, in terms of amount of materials used and ease of use.

SUMMARY OF THE INVENTION

In one aspect, these objects are achieved according to the invention with a pen needle container receiving the patient end and non-patient end of the pen needle in a specified orientation. The container comprises: a first chamber having walls, a closed end, and an opening having edges defining a plane which is aligned with the non-patient end of a pen needle received in the container. A rigid closure attached to and movable with respect to the chamber has a planar member which completely closes off the open end of the chamber in a first position. Attachment means are provided for attaching the closure to the chamber and repeatedly moving the closure from the first position to a second position in which the opening is unobstructed by the closure. A sterility barrier ensuring sterility of the chamber in the first position is broken when the closure is first moved from the first position to the second position. In embodiments, the chamber walls are at 90 degree angles to form a rectangular box. In preferred embodiments, the pen needle is simply a needle-bearing hub adapted for attachment to a medication pen, because the container and closure perform the functions of the outer cover, the inner shield, and the heat-sealed label of a conventional pen needle.

In another aspect of the invention, the attachment means is a hinge formed along an edge of the container perpendicular to the edges defining the opening. In other embodiments, the container is formed like a drawer, so that the attachment means comprises a pair of grooves formed along opposite interior walls of the chamber, cooperating with pins protruding from lateral sides of the closure. The closure may then be swiveled about the pins to provide an unobstructed opening to the chamber.

In another aspect of the invention, the pen needle packaging concept comprises a hub having a needle situated thereon having a patient end and a non-patient end. A cap connected to the hub is formed of first and second ears attached with a hinge. In the closed position of the hinge, the cap encloses both ends of the needle in a sterile enclosure. In the open position of the hinge, the ears of the cap are pressed together by the user, the package is opened, and the non-patient end of the pen needle is exposed. Pressing the halves together to open the hinge may break a sterile barrier, which may be a tortuous path sterile barrier or alternatively an externally applied seal. The user may remove the cap by pulling on the cap after the pen needle is installed on the medication pen.

In embodiments according to this aspect of the invention, the pen needle comprises an inner shield surrounding the patient end of the needle. A protrusion on the interior of the cap mates with a feature formed on the inner shield to stably orient the hub when the cap is pinched open. The inner shield is in turn surrounded by the cap in the closed position and may be disposed so that it is removed with the cap after installation of the pen needle on the medication pen.

Alternatively, the hub may be received with an interference fit in one or the other of the hinged halves of the cap, so that the needle-bearing hub is presented to the user for installation on a medication pen when the packaging is opened.

In another aspect, the pen needle packaging concept is embodied by having caps on opposed ends of the hub which may be held by the user when the pen needle is opened for use. The caps can be mated with the opposed sides of the hub or with each other. The caps can be configured to detach from the hub (or from each other) in a particular order to enhance ease-of-use, such that the non-patient end cap is always removed first. For example, greater force is required to detach the patient end cap from the hub (or from the opposed non-patient end cap) than is required to detach the non-patient end cap from the hub (or the opposed patient end cap). The caps are configured so that the user can hold the pen needle by the patient end cap while removing the non-patient end cap to install the pen needle on a medication pen. The caps may be mated, with a tortuous path barrier for example, to form a sterile enclosure around the needle with a single sterile barrier. In other embodiments of the invention, the patient end cap and the non-patient end cap may form separate sterile enclosures around the patient end needle and non-patient end needle, respectively.

Increasing the force required to detach one cap relative to the force required to detach the other may be accomplished by means known in the art, including without limitation, heat or laser staking, providing different size interference fits, using mechanical snaps or beads, threads, friction welding, using adhesives, or with breakable plastic webs, as described in greater detail below.

In an embodiment according to this aspect of the invention, a disposable pen needle comprises: a hub having a needle situated thereon having a patient end and a non-patient end. A removable patient end cap is attached to the distal end of the hub and a removable non-patient end cap is attached to the proximal end of the hub, overlapping the proximal end of the patient end cap in a single continuous seam, thus forming a single sterile enclosure around the needle.

The pen needle may be provided with one or more tethers connecting the non-patient end cap and the patient end cap to the hub after the seam between the non-patient end cap and the patient end cap has been broken and the respective caps have been detached from one another.

DETAILED DESCRIPTION OF THE INVENTION

As used herein, a "pen needle" according to the invention may consist of only a needle-bearing hub, because the packaging substitutes for the conventional outer cover and tear drop label. The pen needle has a "non-patient" end which is adapted to be attached to a medication pen. When received in the container, the pen needle hub is situated so that the non-patient end is at the opening of the container for easy access by the user, substantially in the plane of the opening. As used herein, the edges which define the opening are said to be "aligned" with the non-patient end of the pen needle in this state. As used herein, the opening to the pen needle chamber is "unobstructed" when the edges defining the opening are free of hinges or any other elements that impede access to the pen needle. "Removable," as used herein, means that a part is intended to be removed by a user during normal use of the device.

In various embodiments the container is in the shape of a box. The sidewalls of the box are said to be at a "90 degree angle," notwithstanding that plastic molding processes may require the corners to be rounded. Likewise, sidewalls of the box meet at "edges," such that three edges of a box meet at a corner. These need not be sharp edges to be considered edges, provided the overall appearance creates an impression of a rectangular box. Terms such as "inward," "inner," and "inside" mean toward or facing the inside of the container, and "outward," "outer" and "outside" have the opposite meaning. The drawings are schematic and not to scale.

The embodiments of the invention described herein are intended to reduce the steps necessary for the user to retrieve a pen needle from its packaging and install it on a medication pen. In the embodiments described herein, a peel-off label closing off an open end of the packaging can be omitted. Instead, opening the container to access the pen needle breaks the sterile barrier. In many cases, the embodiments described below are capable of one-handed operation, so that the user need not handle the pen needle excessively before installing it on the medication pen. The secure packaging makes it possible in many cases to avoid use of the inner shield used in current packaging. The container itself may act as both a shield and as a sharps container after use.

Figure 1A:
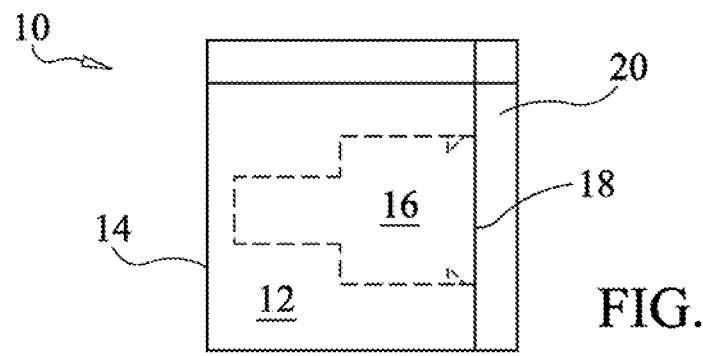
FIG. 1A is a schematic view of a pen needle container according to an embodiment of the invention.

In one embodiment of the invention, depicted in schematic cross section in FIG. 1A, the pen needle container 10 includes a first chamber 12 in the shape of a rectangular box or cuboid. An internal space 16 for receiving the pen needle is oriented so that the patient end is toward the closed end 14 of the container. Opposite the closed end is an open end 18 which is completely closed off by closure 20 in an initial state. The closure is sealed to the container with a sterile barrier (not shown in FIG. 1). The shape of the internal space 16 in the container mirrors the shape of the pen needle, so that the pen needle is stowed securely.

Figure 1B:
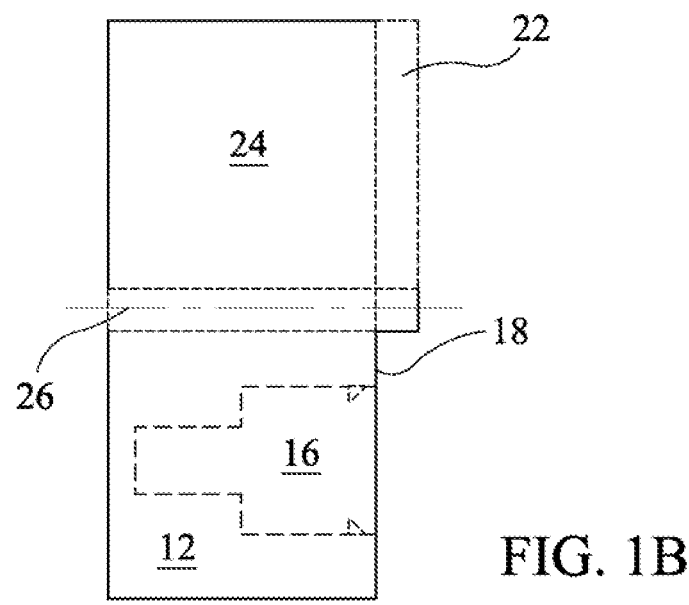
FIG. 1B is a view of the embodiment of FIG. 1A in an open position.

FIG. 1B depicts the embodiment of FIG. 1A in a second, open position. As seen in FIG. 1B, closure 20 is L-shaped, having a first planar member 22 which closes off the open end 18 of the chamber 12, and a second planar member 24, attached to an edge of the first planar member. The second planar member 24 is attached by hinge 26 along an edge of the chamber perpendicular to the edges of the open end 18. Attaching the second planar member to the chamber and the first planar member 22 in this way allows the closure to be manipulated easily by a user with one hand and also allows the open end 18 of the chamber to be completely unobstructed in the open state. A sterile barrier may be applied on a seam formed by the closure 20 and the open end 18 of the pen needle chamber. The sterile barrier is broken when the packaging is opened, which may be done one-handed, leaving no remnants of the barrier on the edges of the open end of 18 of the chamber.

Figure 1C:
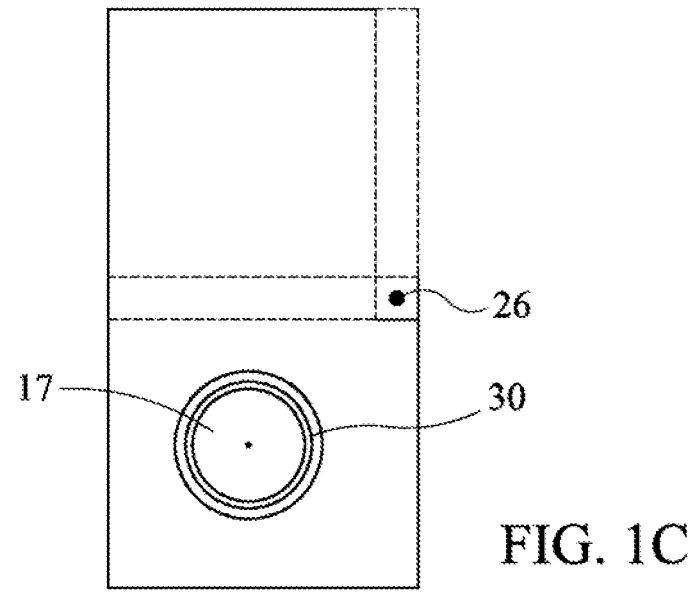
FIG. 1C is a view of the embodiment of FIG. 1A rotated to depict the view into the open end of the container, with the pen needle aligned to the opening.

FIG. 1C depicts the chamber of the embodiment of FIG. 1A in cross section in the second, open, position as seen from the open end 18 of FIG. 1B. In this position, the pen needle hub 30 is exposed, including the non-patient end needle 17, so that the medication pen can be attached to the needle hub while the user holds the container.

Figure 2A:
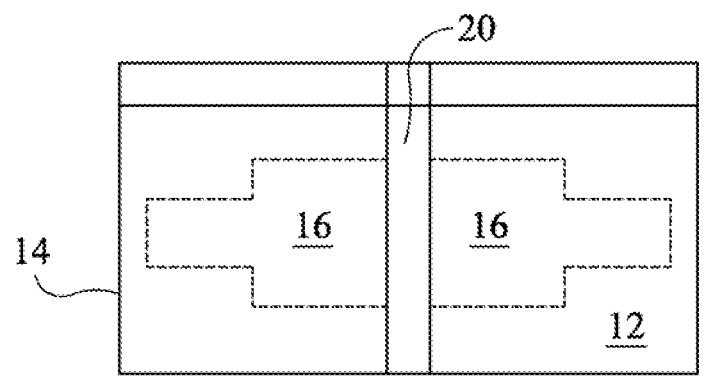
FIG. 2A is a schematic view of an embodiment of the invention in which multiple chambers are combined in a container system.
Figure 2B:
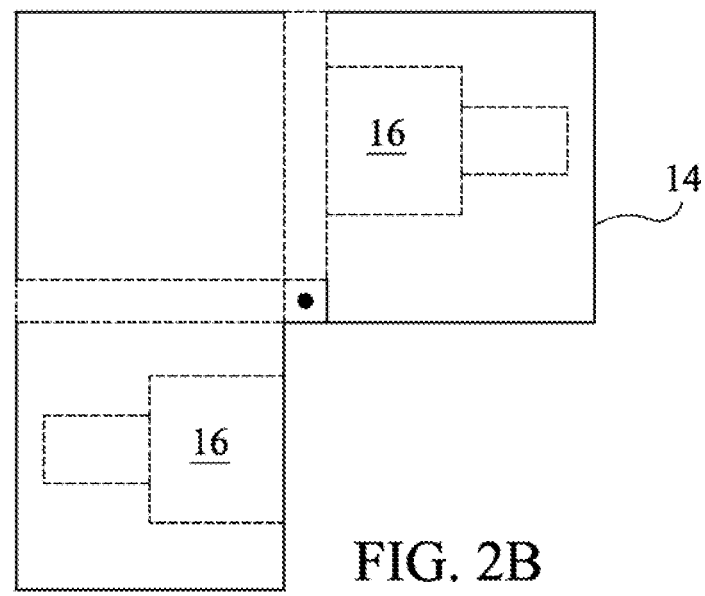
FIG. 2B depicts the embodiment of FIG. 2A in the open position.

Multiple containers similar to that shown in FIG. 1A may be attached, as shown in the embodiment of FIG. 2A and FIG. 2B, and the one-piece or unitary closure 20 completely closes off the open ends of the respective chambers 12 in the first position. As with the embodiment of FIG. 1A, the action of opening the closure is a single handed operation which breaks a sterile barrier formed along the seam between the closure and the open end of the container. The increased size of the assembled containers in the embodiment of FIG. 2A and FIG. 2B is expected to make the container easy to manipulate.

Figure 3A:
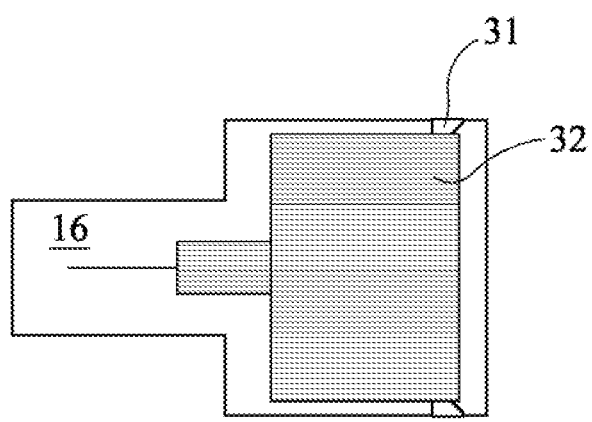
FIG. 3A depicts a re-use prevention mechanism according to an embodiment of the invention in a first position.
Figure 3B:
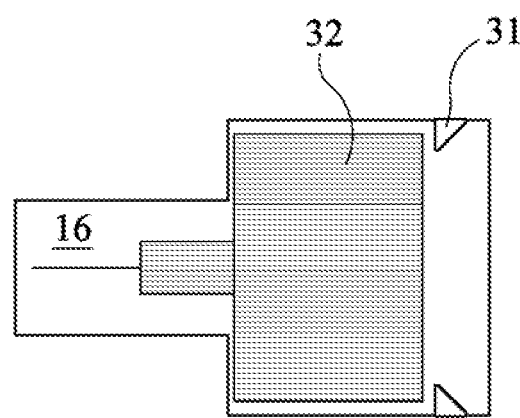
FIG. 3B depicts the re-use prevention mechanism in a second position.

FIG. 3A and FIG. 3B depict a re-use prevention mechanism which can be used with multiple embodiments according to the invention. In an initial position, pen needle assembly 32 is stowed in internal space 16. Two tapered stops 31 having inclined surfaces sloped toward the inside of the container prevent the pen needle from moving in the internal space. After attachment to a medication pen, the pen needle may be slid out of the container by the user. To use the packaging as a sharps container, the user inserts the pen needle past the tapered stops 31, as shown in FIG. 3B, such that the pen needle cannot be easily removed by the user. The pen needle need not be handled by the user when installing the medication pen and the "inner shield" conventionally provided with a pen needle may be omitted.

Figure 4A:
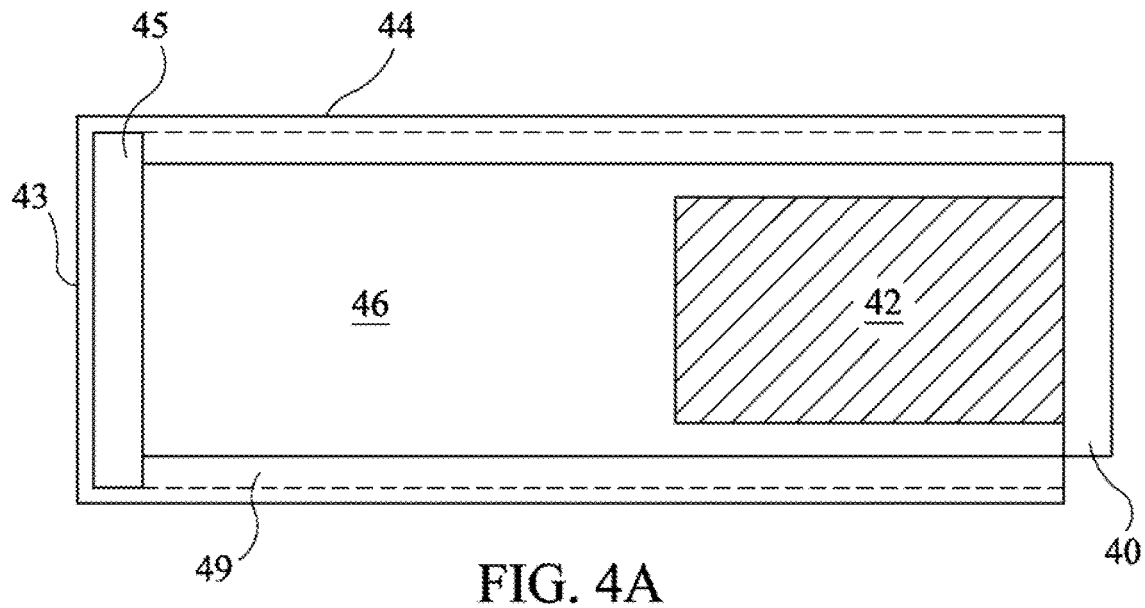
FIG. 4A depicts a top view of a drawer-style embodiment of the pen needle packaging concept according to the invention.
Figure 4B:
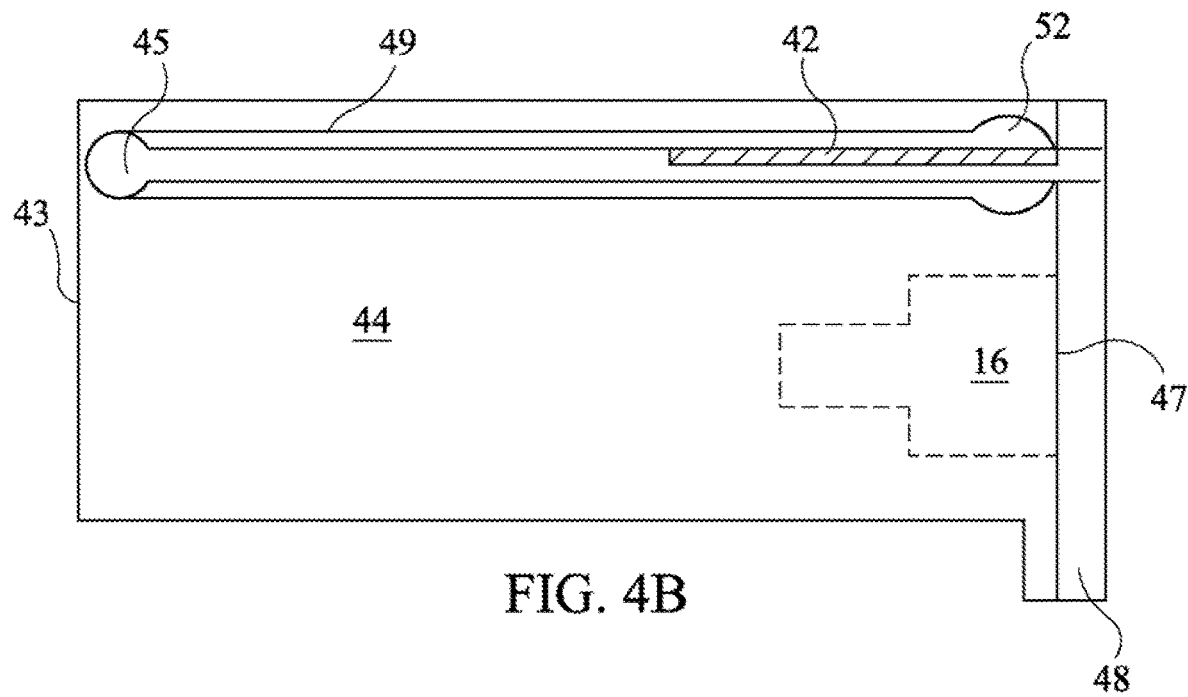
FIG. 4B depicts a side view of the embodiment of FIG. 4A.
Figure 4C:
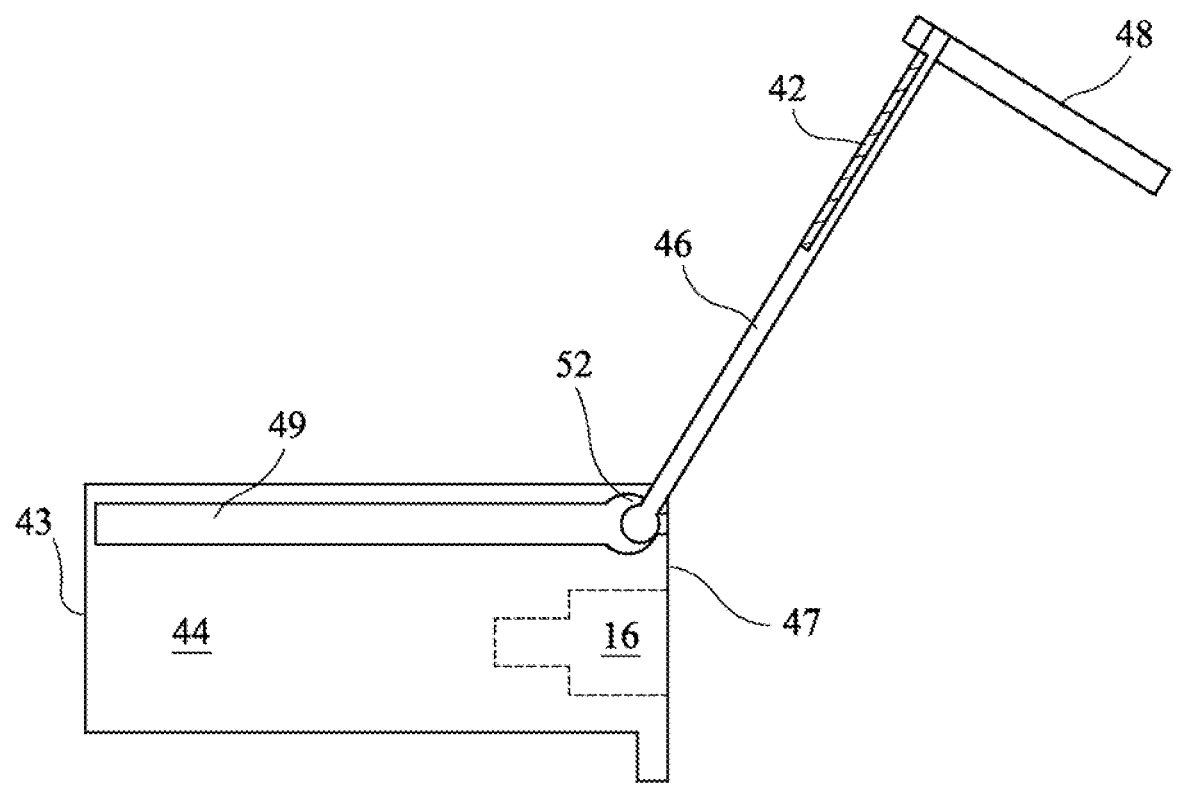
FIG. 4C depicts the container packaging embodiment of FIG. 4A and FIG. 4B in the open position.

In another embodiment, depicted in FIGS. 4A, 4B, and 4C, the pen needle packaging according to the invention includes a drawer-style closure which is received in container 44. As with the previous embodiment, the container is a rectangular box or cuboid. Closure 40 is L-shaped and includes top member 46 and first planar member 48, which completely closes off the open end 47 of the container when the container is closed. The top view is shown in FIG. 4A, wherein the pen needle is accessed by sliding the top member 46 along grooves 49 formed in the side walls of the container. The pen needle internal space 16 may be situated as shown in the side view of FIG. 4B, opposite the closed end 43. The container 44 includes a closed end 43 and an open end 47 opposite the closed end where internal space 16 for receiving the pen needle is situated. The non-patient end of the pen needle is substantially flush with the plane defined by the edges of the open end 47. The seam where the first planar member 48 meets the container 44 may be sealed with a sterile barrier in the closed position. The top member 46 of the L-shaped closure 40 is provided with pins 45 protruding from opposite lateral sides thereof which are received in grooves 49 in the inner side walls of the container 44.

The side view of FIG. 4B depicts pins 45 received in grooves 49 formed in the inner side walls of the chamber 44. The grooves 49 terminate in a portion 52 wider than the rest of the groove. The wider portion 52 permits the closure 40 to be rotated, pivoting about the wider portion 52, so that the planar member 48 is rotated away from the opening 47 and the opening is completely unobstructed in the open position, as shown in FIG. 4C.

In the specific embodiment shown, which is not to be deemed as limiting the invention, the grooves 49 are parallel to the top edge of the chamber 44 where two walls of the chamber meet. In other embodiments, such as depicted in FIGS. 5A and 5B, 6A and 6B, 7A and 7B, and 8A and 8B, the grooves 49 may be oriented diagonally on the side walls of the container, or the grooves may have a bend, with a section parallel to the edges of the box and a section oriented diagonally on the side of the box.

Figure 5A:
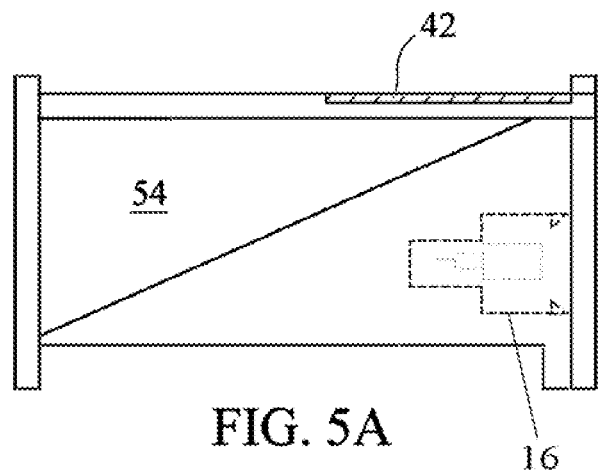
FIG. 5A depicts another embodiment of the invention in the closed position.
Figure 5B:
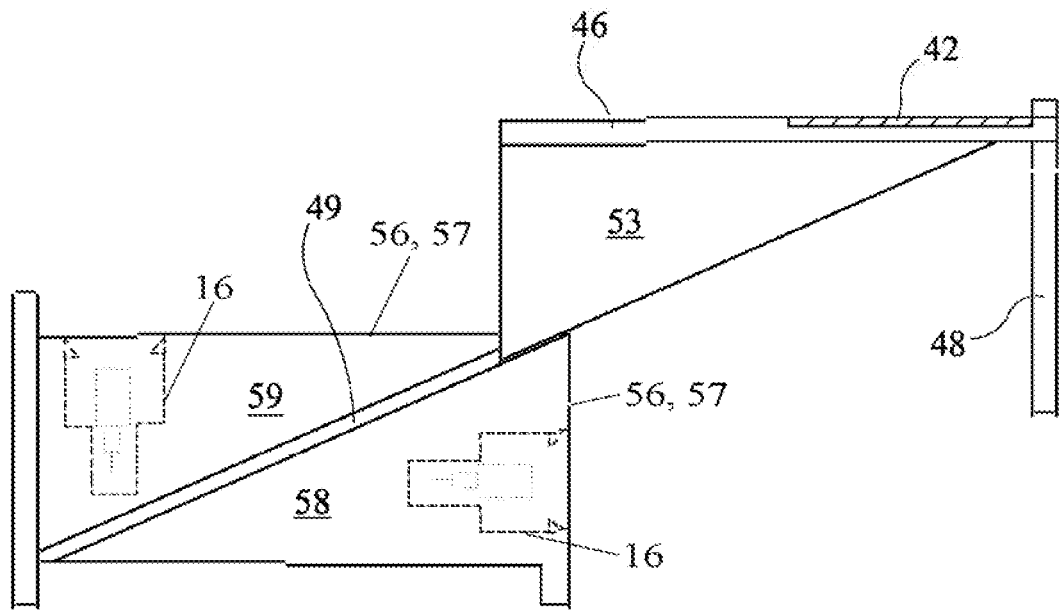
FIG. 5B depicts the embodiment of FIG. 5A in an open position.

The closure may also be embodied as an outer shell or cover as shown in FIGS. 5A and 5B. In the embodiment of FIG. 5A, pins (not shown) protrude inwardly, toward the chamber, from opposite lateral sides of cover 54. Cover 54 comprises a top surface 46 and side surfaces 53 perpendicular to the top surface, with the top and side surfaces all perpendicular to the planar member 48 which closes off an opening for the pen needle internal space 16. Grooves 49 are formed on the outer walls of the chambers 58, 59 to receive the pins, which allows the cover 54 to slide diagonally on the outside of the container.

Multiple chambers 58, 59 may be included in a single container, each having an open end 56 with edges 57 defining a plane. Each chamber 58, 59 includes an internal space 16 for securely receiving a pen needle, as shown in the side view of FIG. 5B. With this configuration, both internal spaces 16 where a pen needle is secured may be unobstructed by a closure without a pivoting arrangement of the cover 54, although the cover may be adapted to pivot as in the previously described embodiment, if desired.

Figure 6A:
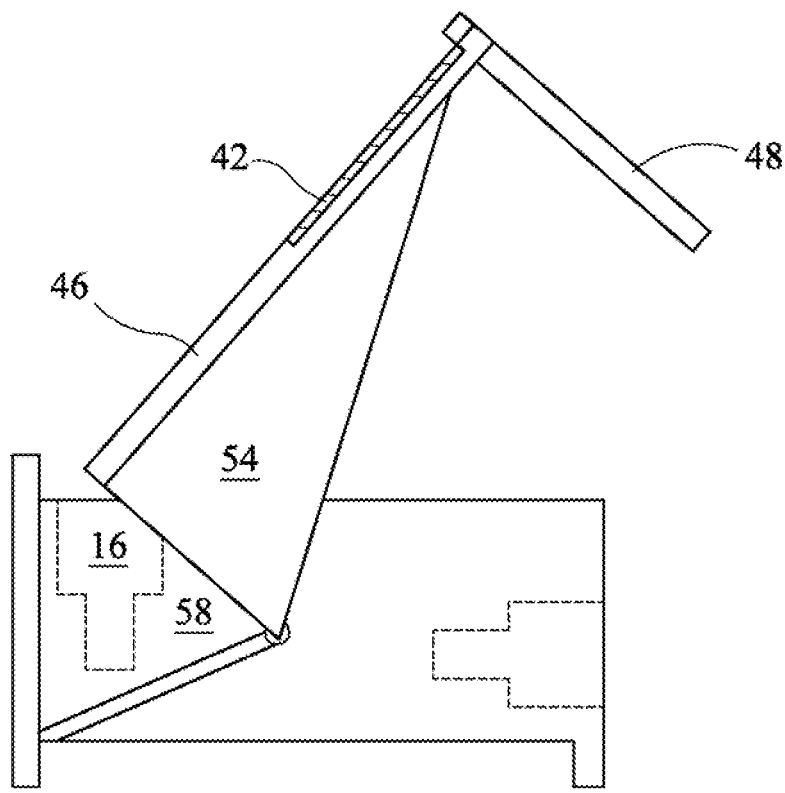
FIG. 6A depicts another embodiment of the invention in the closed position.
Figure 6B:
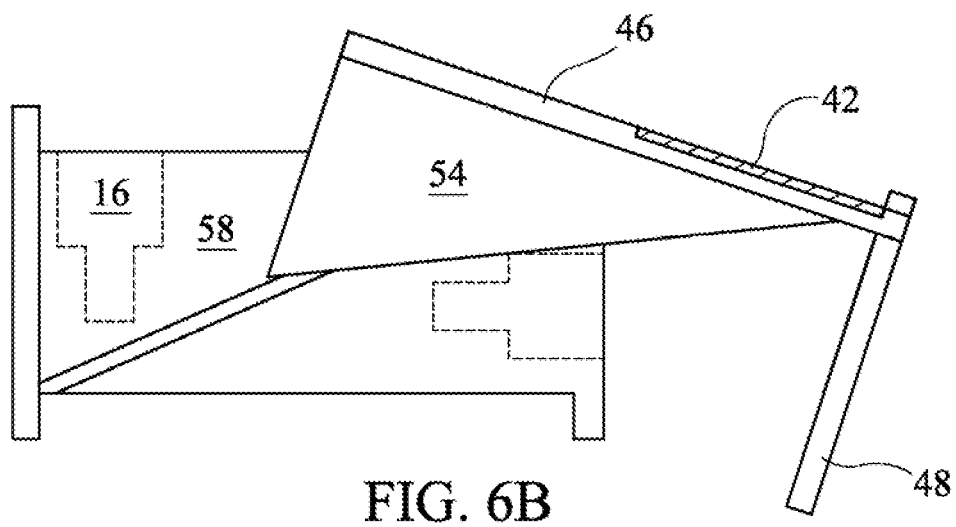
FIG. 6B depicts the embodiment of FIG. 6A in an open position.

In yet another alternative embodiment, as shown in FIG. 6A and FIG. 6B, the diagonal groove extends partially along the outer sidewall of the container, and the cover is provided with the ability to pivot about a point in the middle of the container side wall. As shown in FIG. 6B, this arrangement allows the closure to be manipulated so that the opening(s) of the container are unobstructed by the closure.

Figure 7A:
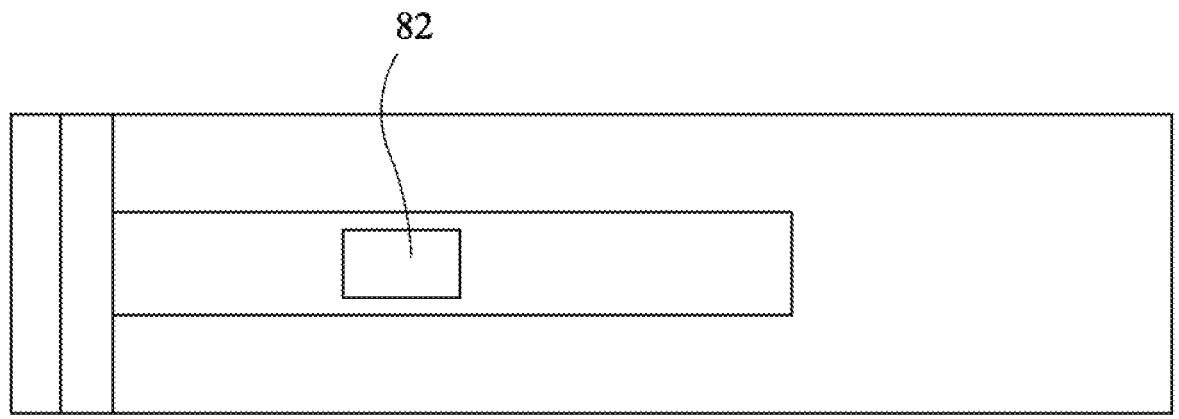
FIG. 7A is a top view of another embodiment according to the invention.
Figure 7B:
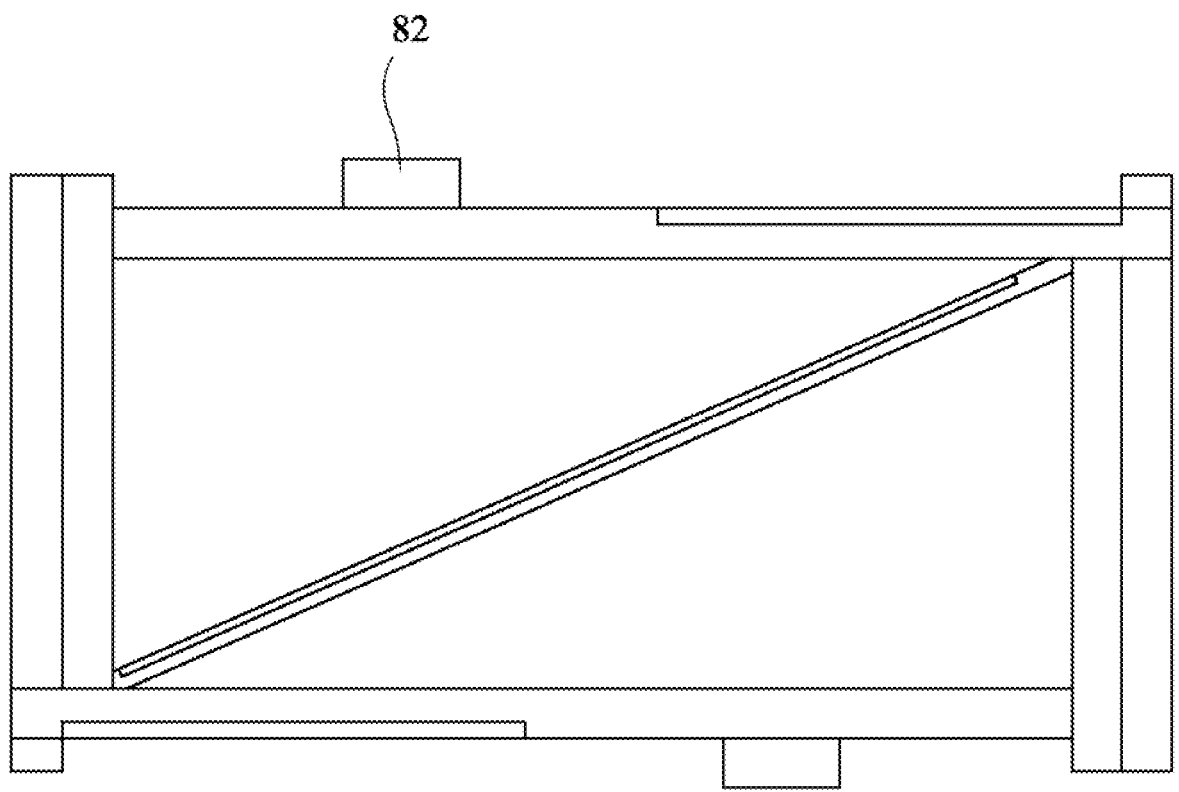
FIG. 7B depicts a side view of the embodiment of FIG. 7A.

For ease of use, in several of the drawer-style embodiments of the packaging according to the invention, a textured portion 42 is provided on the lid, which the user may manipulate with a thumb or other finger to facilitate one handed opening. Textured portion 42 may be used advantageously with any of the closure systems having a sliding top. Likewise, the tapered stops described in connection with FIG. 3A and FIG. 3B, and shown in FIG. 5A and FIG. 5B may be used with any embodiment of the invention described herein so that the container may be used to safely store the pen needle after use. In FIG. 7A and FIG. 7B an additional member 82 on the closure is depicted which provides a grip for the users' fingers to push against when opening the container, in addition to, or as an alternative to, the textured portion 42.

Figure 8A:
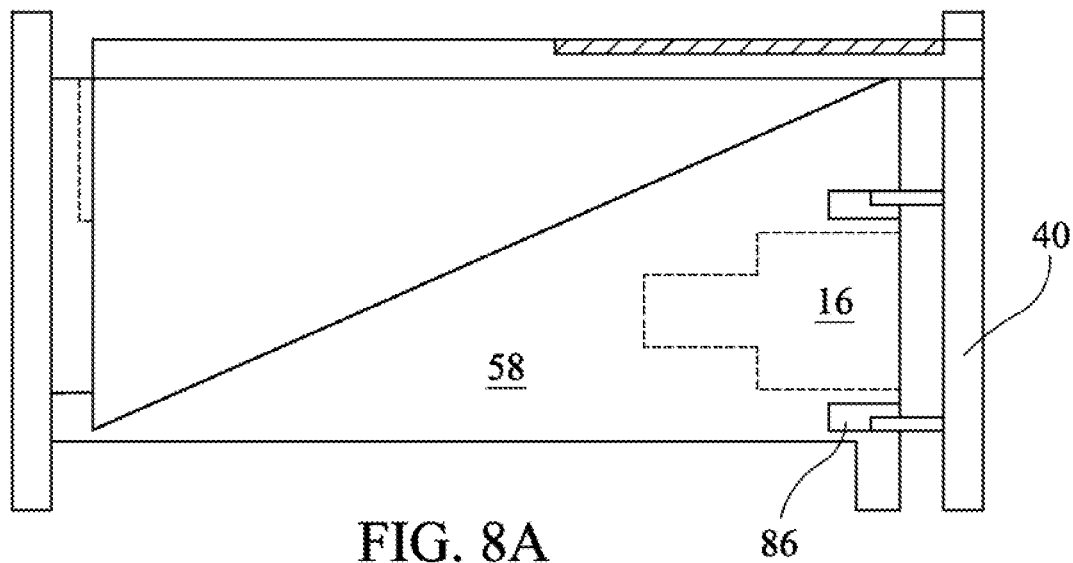
FIG. 8A depicts a sterile closure system according to an embodiment of the invention.
Figure 8B:
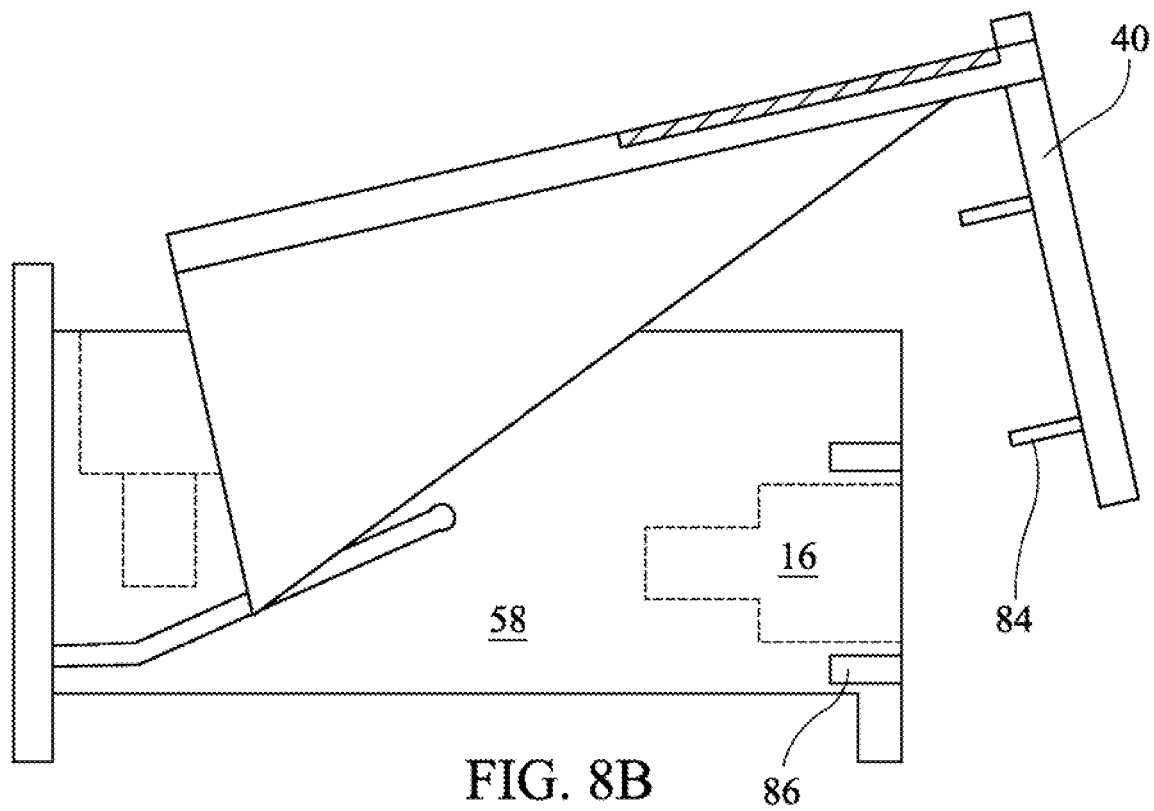
FIG. 8B depicts the embodiment of FIG. 8A in the fully open position.

Sterility of the cannula may be maintained by presenting a tortuous path to airborne microorganisms between the outside of the container and the pen needle space 16. For example, in FIGS. 8A and 8B, sterility can be maintained by providing matching tortuous path faces on the cover 40 and the chamber 58. In FIG. 8A and FIG. 8B a pair of mating features, such as ring 84 and receiving recess 86 provide the necessary tortuous path. A straight portion of the groove on the side of the container permits the mating features 84, 86 to detach when the container is initially opened and before the pivoting motion begins.

Figure 8C:
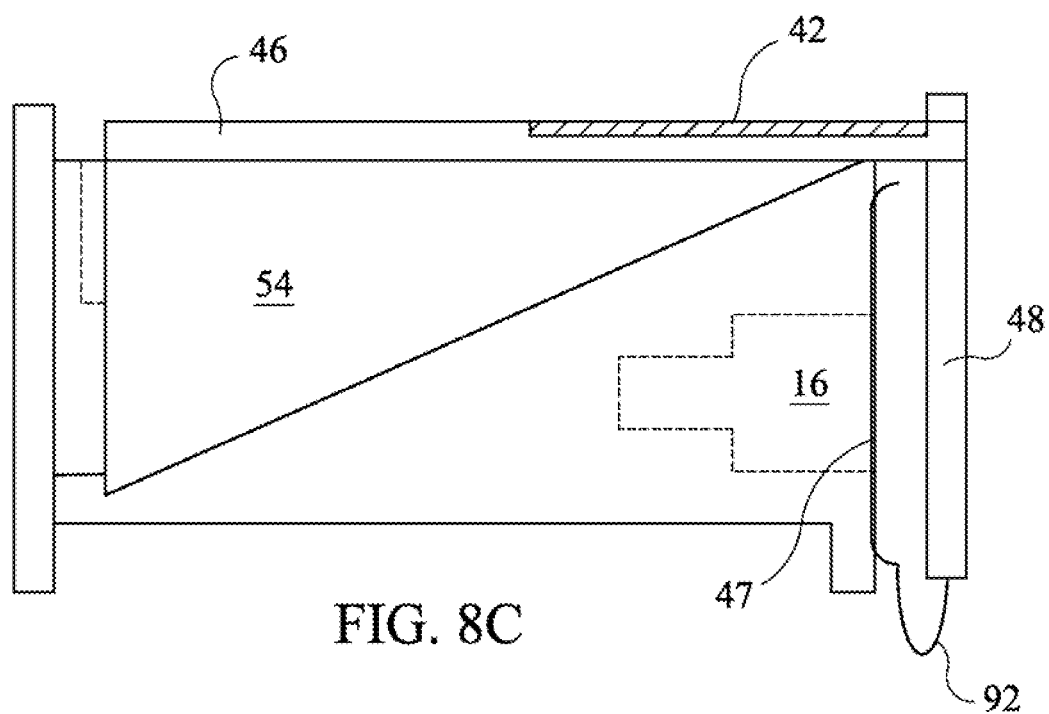
FIG. 8C depicts a sterile closure system according to another embodiment of the invention.
Figure 8D:
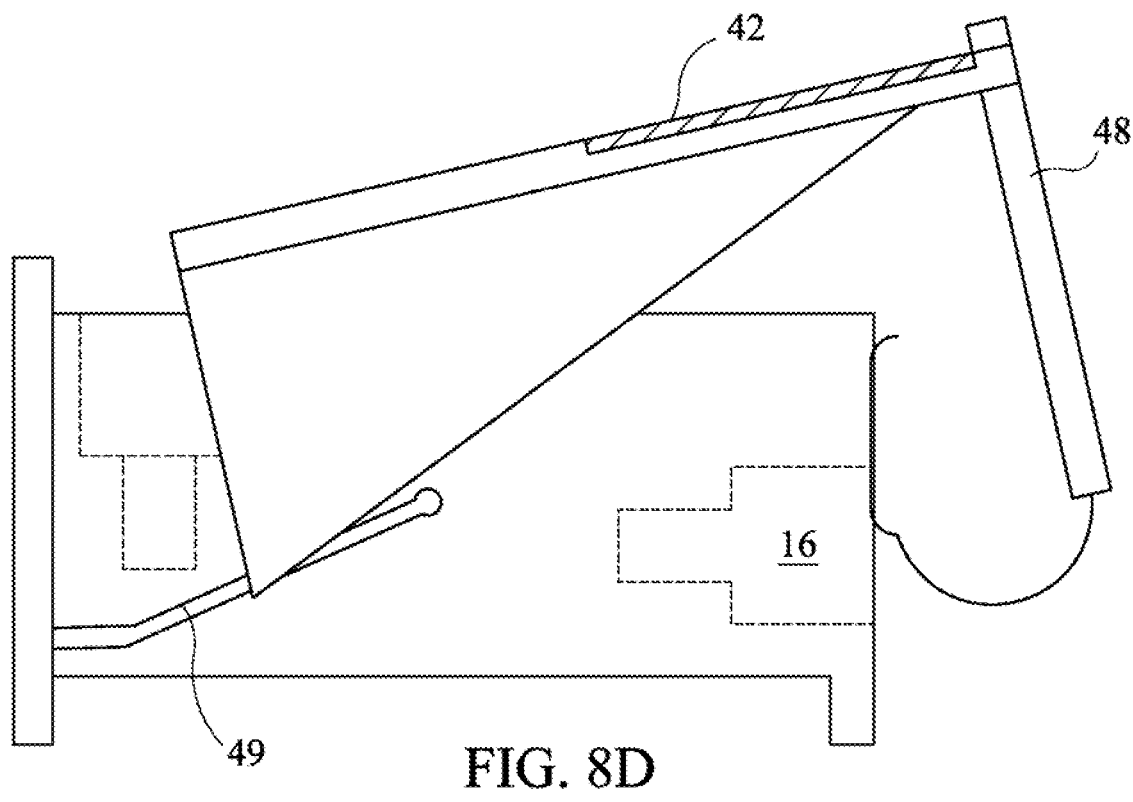
FIG. 8D depicts the embodiment of FIG. 8C as the sterile closure is opened.

FIG. 8C and FIG. 8D depict an alternative sterility barrier in which a film barrier is sealed across the open end of the pen needle chamber 16. The film 92 is attached the planar member 48 of the closure. When the planar member 48 is pivoted away from the open end of the chamber, the film 92 is peeled automatically from the opening. In this manner, the single act of opening the container performs the functions of removing the sterility barrier and allowing access to the pen needle via an unobstructed opening. As with the previous embodiments, a separate step of peeling a label to provide access to the pen needle is omitted.

In another aspect, the invention pertains to pen needle packaging which permits the user to squeeze one end of the pen needle packaging on the patient-end side of the assembly, which in turn breaks open the opposite end of the packaging to expose the non-patient end of the pen needle for attachment to a medication pen.

Figure 9:
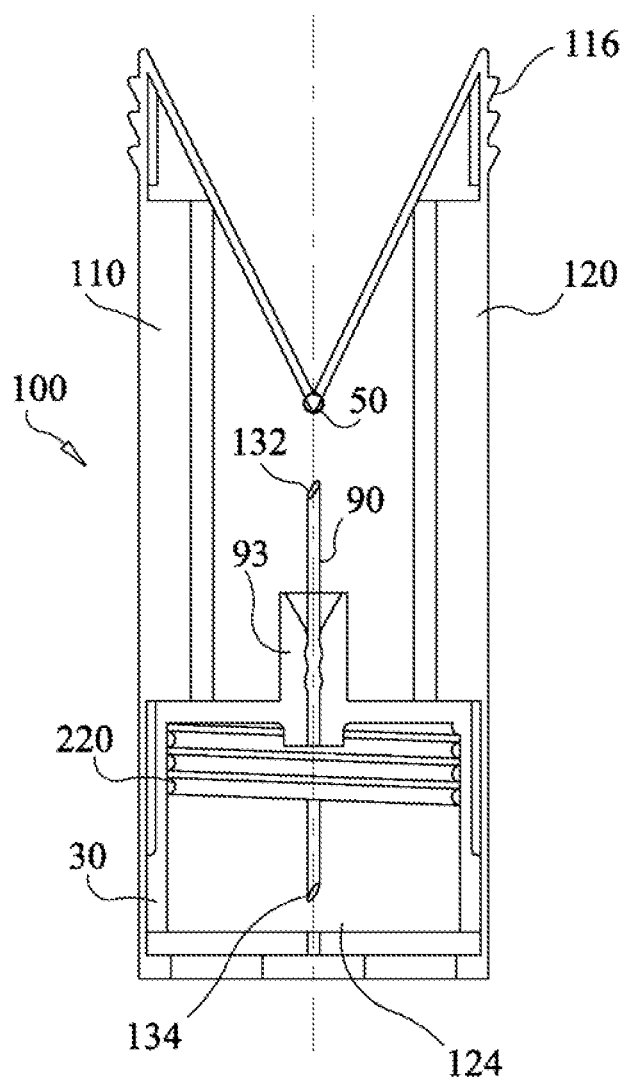
FIG. 9 is a cross sectional view of pen needle packaging according to an embodiment of the invention in the closed state.
Figure 10:
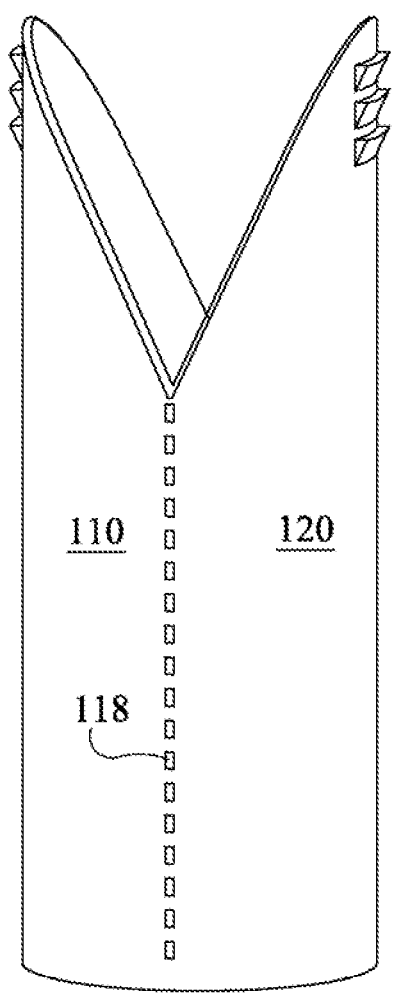
FIG. 10 depicts the outside of the pen needle packaging according to the embodiment of FIG. 9.
Figure 11:
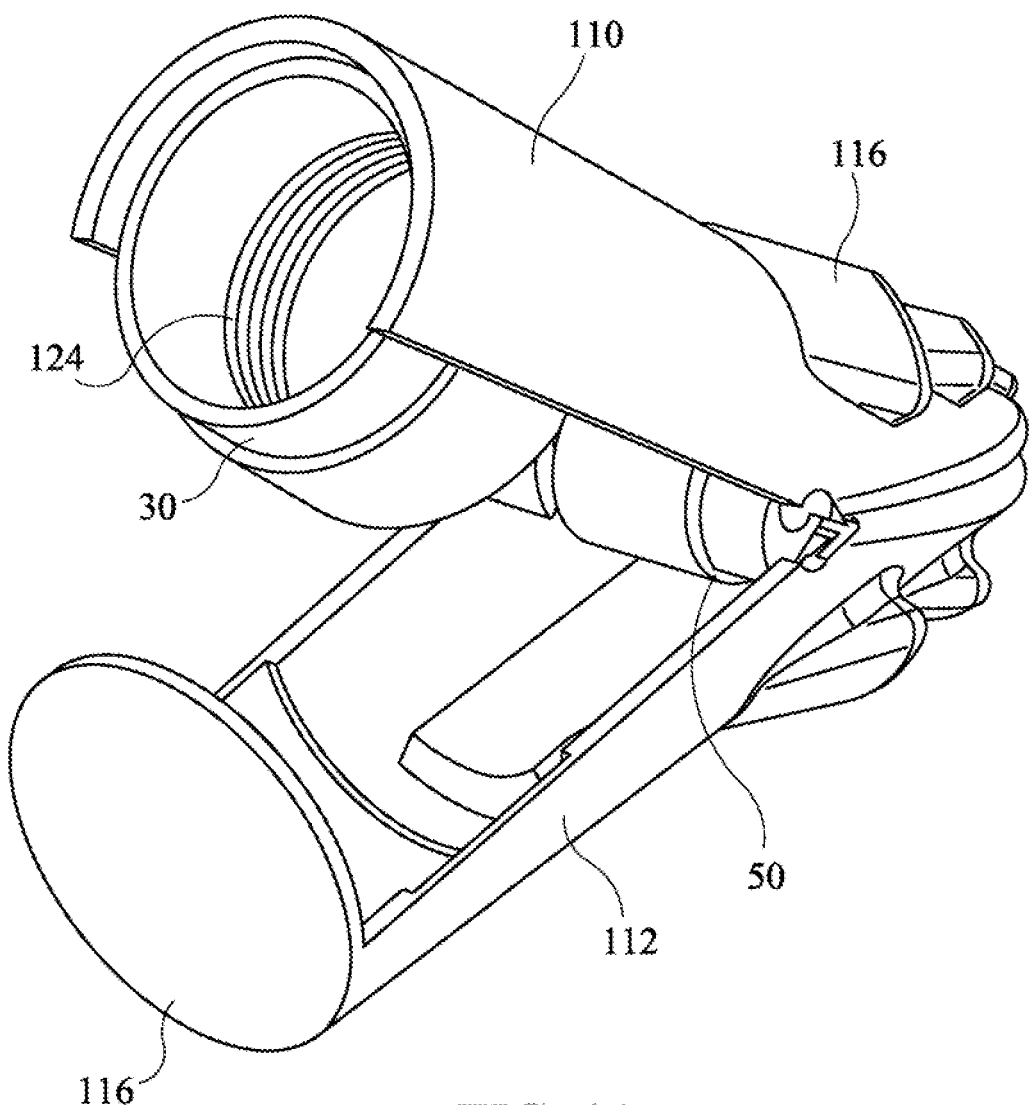
FIG. 11 depicts the pen needle packaging according to FIG. 9 in the open state.

In the cross-sectional view of FIG. 9, pen needle hub 30 has a needle 90 situated thereon having a patient end 132 and a non-patient end 134. Opening 124 on the non-patient end of the hub is provided with threads 220 for installation of the pen needle on a medication pen. Cap 100 is formed of first and second ears 110, 120 attached with a hinge 50. The ears 110, 120 constitute halves of the closed cap structure. Hinge may be of any type, such as a "living hinge," or coiled flexible strip as shown in FIG. 11. First and second ears 110, 120 may be provided with textured surfaces 16, which the user can grasp to pinch the ears together to provide more ergonomic packaging. The hinge is shown in the closed position in FIG. 9 and FIG. 10, with the patient end and the non-patient end of the needle enclosed in a sterile enclosure. It is preferable that the end of the cap with the ears extends from the distal side of the hub, beyond the patient end of the needle.

Sterility may be maintained by a providing a tortuous path for the closure of ears 110, 120, such as step shapes on the respective ears that engage when the ears are closed to present a tortuous path that prevents airborne microorganisms from entering the sterile space around patient end needle 132. Alternatively, a label over the seam between the two halves may be used to form a sterile barrier. In either case, the ears are adapted to open along seam 18, shown in FIG. 10, and preferably, the halves are burst open by the user pinching the ears. For this purpose, the seam 18 may be nearly perforated, but not punched through, so that the packaging can be burst open, but sterility is maintained. If desired, the halves of the cap may be provided with mating elements so that the cap can be locked shut after use. In this way, the cap according to the invention can be used as a sharps container.

This packaging concept has the advantage of reducing the number of steps required to access and use the pen needle. Rather than having to remove a teardrop label, as in existing commercial embodiments, the configuration according to the invention can be opened with one hand by squeezing one end of the cover. After opening, the open end 124 of the pen needle is accessible for attachment to the medication pen. In FIG. 11, the pen needle is cradled in one of the halves in an interference fit when the cap is pinched apart. In another embodiment (not shown), a removable inner shield is fitted over the patient end of the needle around post 93 on the hub. The inner shield can contact a feature provided on the cap to retain the needle bearing hub in a central position using the post 93 on the hub.

The flexible front end cap has other advantages over the conventional pen needle sealed with tear drop label, in that similarly shaped packaging units may be nested. Thus, the space between ears 110, 120 may receive the non-patient end of another cap, so that a series of similar caps can be provided in a dispenser, for example.

Figure 12:
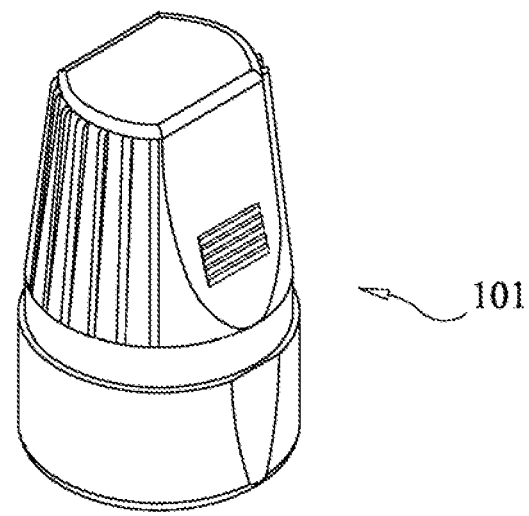
FIG. 12 depicts a pen needle with mating caps according to an embodiment of the invention in a sealed state.

In another aspect of the invention, the pen needle packaging is configured to be gripped by the user and opened so that the non-patient closure breaks away first, exposing the non-patient side of the pen needle for installation on a medication pen. In the embodiment depicted in FIG. 12, the pen needle is provided with outer caps that seal to the pen needle hub, or to each other, to provide a sterile enclosure around the pen needle. Sterility can be maintained using a tortuous path formed by the overlapping of the caps, and/or a barrier label can be formed over the seam between the caps. The mating of the caps can be configured so that the non-patient end of the hub is presented to the user ready for installation on a medication pen when the sterility barrier is broken. The concept of a tortuous path or labyrinth seal to preserve sterility is well known in the biomedical devices art, and simply means that airborne organisms are presented with a tortuous path which prevents the organisms from contaminating the enclosed space around the cannula. In the closure described above, the barrier forms a type of seal which must be broken by the user before use, but the force required is not so great as to cause inconvenience. The concept of the labyrinth seal is elaborated upon in U.S. Patent Application Publication No. 2012/0041381, incorporated by reference.

Figure 13:
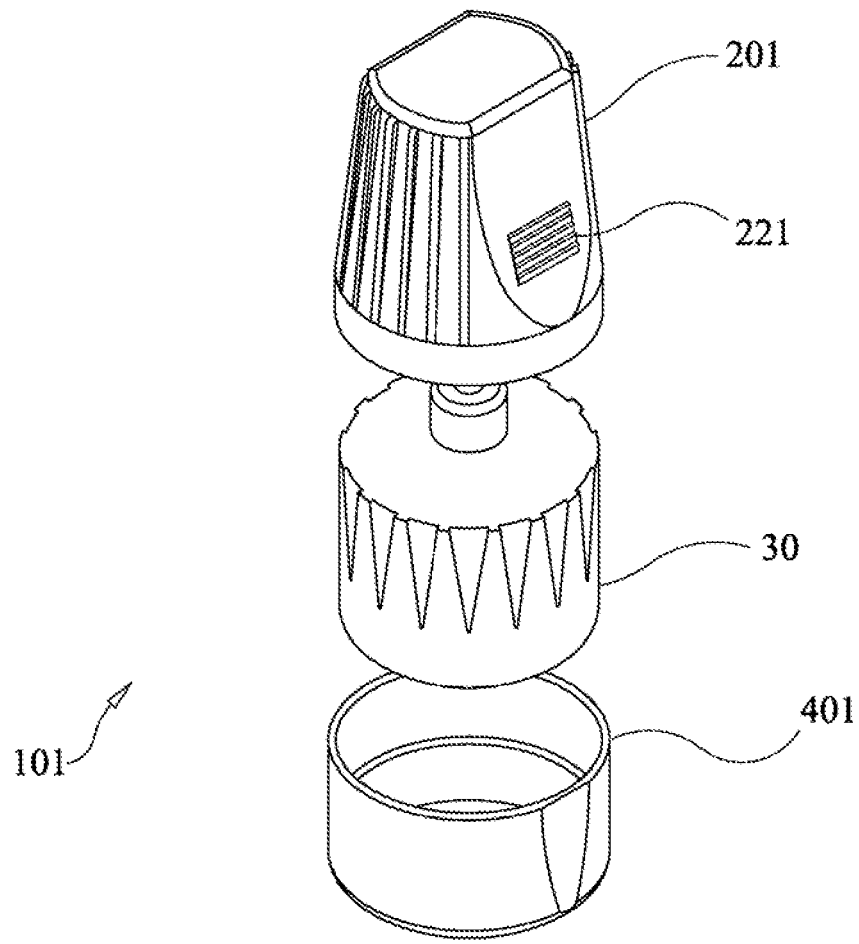
FIG. 13 is an exploded view of the pen needle of FIG. 12.

In the exploded view of FIG. 13, patient end cap 201 is shown fitting over the needle cannula on the patient side of the hub 30, and non-patient end cap 401 fits over the non-patient side of the hub. In the conventional designs, the entire hub is inserted into a single cap, and the open end of the cap is closed off with a sterile tear drop label. Typically, an inner shield is positioned between the needle cannula and the cap. The shorter patient end cap of the present embodiment eliminates the tear drop label and the conventional inner shield and reduces overall material usage.

To improve ease-of-use, patient end cap 201 may be provided with a textured surface 221 for the user to grasp.

Figure 14:
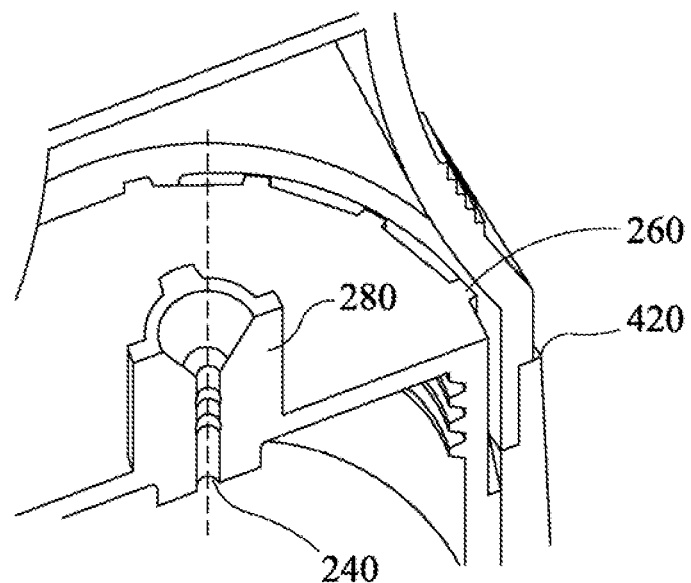
FIG. 14 is a detail depicting the engagement of the patient end cap and the hub.
Figure 15:
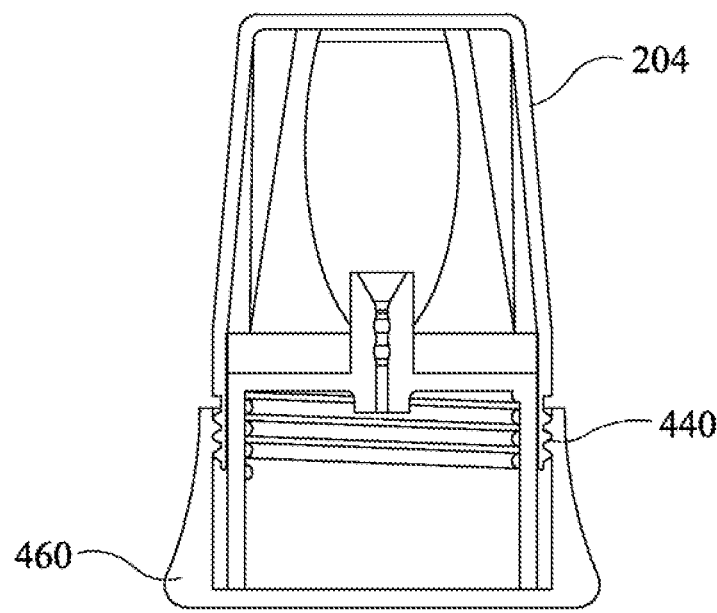
FIG. 15 depicts an alternative embodiment with a threaded engagement of the caps.

Referring to FIG. 15, a grip in the form of wings 460 may be provided on the non-patient end cap to improve ergonomics. The use of the textured surface or shaped non-patient end cap is not limited to the embodiment of FIG. 12 through FIG. 15.

In another embodiment, the non-patient end cap and the patient end cap each form a separate sterile barrier around the respective needles. To ensure that the non-patient end cap is detached first, the patient end cap may be attached to the hub using staking, whereby a protrusion on the hub or cap is mated with a corresponding dimple in the other element and then the dimple is conformed around the protrusion using heat or laser. An attachment means requiring less force, such as a slight interference fit may be provided between the hub and the non-patient end cap on the proximal end of the hub. Many other means are available to ensure that a greater force is required to detach the patient end cap from the hub relative to the non-patient end cap. For example, the cap on the patient end side may be attached with threading. Staking can be applied to the attachment of the caps on both sides of the hub, provided that the patient end side is staked more securely. Likewise, different interference fits can be employed on both sides of the hub. The forced order of opening the cap ensures that the user handles the patient-end of the pen needle by its outer cap during installation and reduces the likelihood of accidental needle sticks.

FIG. 14 depicts another example in which the caps are configured so that the non-patient end cap 40 pulls away first from the hub 30 when the caps are separated. For this purpose one or more protrusions 260 on the hub mates with a corresponding feature on the inside of the patient end cap 201. Consequently, a slightly increased force is required to separate the patient end cap from the hub, while the non-patient end cap 420 is mated with the patient end cap 201 with an interference fit. Thus, during use, the non-patient end cap is removed first, allowing a user to expose the threads on the hub for installation on a medication pen before the patient end cap is removed to expose the patient end cannula. This feature further obviates the need for a shield inside the patient end cap—reducing the number of accidental needle sticks while enhancing ease-of-use.

Sterility of the enclosure formed by the mated caps may be maintained by providing a tortuous path where cap 420 meets the patient end cap at the single continuous seam between the two caps, as shown in FIG. 14. Alternatively, a label is used over the single seam to preserve stability. According to another embodiment depicted in FIG. 15, the patient end and non-patient end caps are mated via a threaded connection 440, which also serves as a tortuous path sterility barrier.

The same container may be configured so that the hub can be recapped and the two opposed caps 201 and 401 can be locked. Thus the mated caps act as a sharps container after use. The locking of the caps can be achieved in a variety of ways known in the art, such as by providing a finger inside one of the caps and a corresponding groove on the other which traps the finger. The user rotates the caps relative to one another to align the finger with the groove. So called "irreversible" interlocking arrangements in a similar context are known in the art. A locking enclosure has the advantage that the user can determine when the device is to be permanently locked, which in some instances is preferred to an automated lock-out achieved with a passively shielded pen needle.

Any material or method known in the art may be used to manufacture the hub and caps. Plastic injection molding is the presently preferred method. Using a molding technique, the caps may be formed with a tether, a strip of material connecting each cap to the hub. With this embodiment (not shown in the FIGS), the two caps may be formed as a single molded part. Left on the product, the tethers reduce the chance that a user loses a cap during use. Alternatively, the tethers may be cleaved from the product during assembly.

The above description of the preferred embodiments is not to be deemed limiting of the invention, which is defined by the following claims. The foregoing description should provide the artisan of ordinary skill with sufficient information to practice variants of the embodiments described. Features and improvements described in connection with one embodiment or with one independent claim may be combined with other embodiments or another independent claim without departing from the scope of the invention described.

The invention claimed is:

1. A disposable pen needle, comprising:
   a hub having a needle situated thereon having a patient end and a non-patient end;
   a removable patient end cap attached at the distal end of the hub;
   a removable non-patient end cap attached at the proximal end of the hub; wherein greater force is required to detach the patient end cap than is required to detach the non-patient end cap.

2. The disposable pen needle according to claim 1, further comprising
   a single continuous seam between the patient end cap and the non-patient end cap forming a sterile enclosure around the needle.

3. The disposable pen needle according to claim 2, wherein the continuous seam creates a tortuous path barrier forming a sterile enclosure around the needle.

4. The disposable pen needle according to claim 2, wherein a label is disposed over the single continuous seam to preserve stability.

5. The disposable pen needle according to claim 1, wherein the patient end and non-patient end caps are mated via a threaded connection, which creates as a tortuous path sterility barrier.

6. The disposable pen needle according to claim 1, wherein the non-patient end cap and the patient end cap each form a separate sterile enclosure around the non-patient end needle and patient end needle, respectively, on opposite sides of the hub.

7. The disposable pen needle according to claim 1, wherein the non-patient end cap and/or the patient end cap is attached to the hub by at least one means selected from heat staking, threaded connection, breakable plastic webs, interference fit, adhesive, and friction welding.

8. The disposable pen needle according to claim 1, further comprising:
   an interference fit between the hub and the non-patient end cap; and
   mating protrusions on the inside of the patient end cap and the outside of the hub engaging the hub and resulting in increased force required to separate the hub from the patient end cover relative to the force required to separate the hub from the non-patient end cover.

9. The disposable pen needle according to claim 1, further comprising tethers connecting the non-patient end cap and the patient end cap to the hub after the seam between the non-patient end cap and the patient end cap is broken and the respective caps are detached from one another.

10. The disposable pen needle according to claim 1, comprising a threaded mating connection between the patient end cap and the non-patient end cap.

11. The disposable pen needle according to claim 1, wherein the patient end cap and the non-patient end cap are configured to lock together to enclose the hub after use.

12. The disposable pen needle according to claim 11, wherein the patient end cap and the non-patient end cap are configured to be permanently locked upon engagement.

13. The disposable pen needle according to claim 1, wherein a tear drop label and an inner shield are not present.

* * * * *